(12) United States Patent
Ghebre-Sellassie et al.

(10) Patent No.: US 6,677,362 B1
(45) Date of Patent: Jan. 13, 2004

(54) SOLID PHARMACEUTICAL DISPERSIONS

(75) Inventors: Isaac Ghebre-Sellassie, Morris Plains, NJ (US); Robert Reisch, Jr., Butler, NJ (US); Riten Parikh, Randolph, NJ (US); Mahdi B. Fawzi, Flanders, NJ (US); Russell U. Nesbitt, Somerville, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 08/218,495

(22) Filed: Mar. 28, 1994

Related U.S. Application Data

(63) Continuation of application No. 07/809,656, filed on Dec. 18, 1991.

(51) Int. Cl.$^7$ .......................... A61K 31/425; A61K 9/14
(52) U.S. Cl. .................. 514/369; 424/486; 424/487
(58) Field of Search .................. 514/369; 424/486, 424/487

(56) References Cited

U.S. PATENT DOCUMENTS

| | | | | |
|---|---|---|---|---|
| 4,572,912 A | * | 2/1986 | Yoshioka et al. | 514/369 |
| 4,801,460 A | | 1/1989 | Goertz et al. | 424/468 |
| 4,917,893 A | * | 4/1990 | Okada et al. | 424/423 |
| 4,980,378 A | * | 12/1990 | Wong et al. | 514/785 |
| 4,996,193 A | * | 2/1991 | Hewitt et al. | 514/11 |

FOREIGN PATENT DOCUMENTS

| | | | | |
|---|---|---|---|---|
| EP | 580860 | 5/1994 | | A61K/9/14 |
| WO | 182341 | 9/1978 | | |
| WO | WO 8300091 | 1/1983 | | A61C/15/03 |
| WO | WO 9006115 | 6/1990 | | |
| WO | WO 9311749 | 6/1993 | | A61K/9/10 |

OTHER PUBLICATIONS

Remington Pharm Sciences, 1985, 17$^{th}$ Ed pp–1603–1615.*
Hand book of Pharm Excepts, 1988, Am Pharm Assoc pp–177–80, 209–216, 225–228, 281–288.*
Bremecker, 1985 103 CA: 1471775.*
Dialog Information Services, file 351, WPIL, Dialog accession No. 007112953, WPI accession No. 87–112950/16, Ichimaru Farcos KK et al: "Formation of solid dispersion or microcapsule containing medicine comprises spray drying solution or suspension formed by stirring alkaline water solution containing medicine and copolymer", JP 62059207, A, 870314, 8716 (Basic) 1997.
Dialog Information Services, file 351, WPIL, Dialog accession No. 009254330, WPI accession No. 92–381747/46, Nippon Shinyaku Co Ltd: "Manufacture of solid dispersion—using twin–screw extruder to form controlled–release pharmaceutical composition without organic solvent, high temp., etc.", WO 9218106, A1, 921029, 9246 (Basic) 1992.

* cited by examiner

*Primary Examiner*—Russell Travers
(74) *Attorney, Agent, or Firm*—Charles W. Ashbrook; Matthew J. Russo

(57) ABSTRACT

A novel solid pharmaceutical dispersion that improves the bioavailability of poorly water soluble drugs is produced by combining the drug with a polymer carrier such as polyvinylpyrrolidone. The drug is combined with the carrier without the need for using organic solvents or melting temperatures (fusion) through the use of a transition compound such as polyethylene glycol which partially solubilizes the drug and/or plasticizes the polymer.

15 Claims, No Drawings

SOLID PHARMACEUTICAL DISPERSIONS

This is a continuation of prior application Ser. No. 07/809,656 filed on Dec. 18, 1991.

BACKGROUND OF THE INVENTION

The bioavailabilities of many poorly water soluble drug entities are limited by their dissolution rates which in turn are governed by the particle size and hence the specific surface area and/or the polymorphic state of the active ingredient. At times, these problems are overcome by particle size reduction. There are cases, however, where the dissolution rates of the drug are not favorable enough to improve its bioavailability. Therefore, techniques such as lyophilization, solvent deposition, solvate formation and solid dispersion have been employed to improve the absorption of drugs.

A solid dispersion is a pharmaceutical formulation which may be defined as "a dispersion of one or more active ingredients in an inert carrier or matrix at solid state prepared by melting the two (fusion), dissolving them in a solvent, or a combination of approaches, i.e., a quasi melting-solvent method". The solvent-based process uses organic solvents to dissolve and intimately disperse the drug and carrier molecules. The process is relatively difficult. Identification of a common solvent for both drug and carrier is a tedious exercise, and complete solvent removal from the product is, if at all possible, a lengthy process. In addition, the volume of solvents required is excessive, and the cost of solvent recovery systems is prohibitive. The drug and carrier are dissolved in a solvent such as methylene chloride, acetone, ethanol and mixtures thereof and the solvent is later removed by evaporation or the like while the drug/carrier solid dispersion is collected as a powdered mass. Not only is the process lengthy and expensive, but the use of organic solvents renders it hazardous and toxic as well.

The second process for the manufacture of pharmaceutical dispersions involves fusion of the two components where the drug and the carrier are allowed to melt at temperatures at or above the melting point of the drug. In the fusion process, the drug and carrier are first blended and melted in a suitable mixer. The molten mixture is then cooled rapidly to provide a congealed mass which is subsequently milled to produce a powder. The fusion process is technically simple provided that the drug and carrier are miscible in the molten state but this is not always the case and furthermore, the process is limited in that it tends to lead to drug decomposition due to the high temperatures required to melt the two components.

A third method that is used to produce a solid dispersion when there is difficulty with thermal instability and immiscibility between the drug and the carrier is the hybrid fusion-solvent method. The drug is first dissolved in a small quantity of organic solvent and added to the molten carrier. The solvent is then evaporated to generate a product that is subsequently milled to produce a powder. The pharmacokinetics, dissolution rates and processes for formulation of many different solid pharmaceutical dispersions is discussed at length in an article by Ford, J., in Pharm. Acta. Helv. 61, 3; 69–88 (1986).

It is an object of the present invention to describe a novel manufacturing process for a solid pharmaceutical dispersion which obviates the need for organic solvents, elevated melting temperatures or the use of both. In particular, it is an object of the present invention to produce a solid pharmaceutical dispersion by incorporating in the formulation a solubilizer/plasticizer which acts as a vehicle to reduce the transition temperature by partially solubilizing the drug and/or plasticizing the polymer. This is particularly useful in the formulation of solid pharmaceutical dispersions for drugs that decompose at or near their melting temperatures.

U.S. Pat. No. 4,803,081 to Falk et al. discloses an extended release preparation of an active compound with very low solubility wherein the compound is dispersed in a liquid or semi-solid non-ionic solubilizer such as esters and ethers of polyethylene glycols. The solubilized drug is then combined with a hydrophilic gel system which controls the release of the drug and solubilizer at a constant even rate.

U.S. Pat. No. 4,689,235 to Barnes et al. discloses an extrudable encapsulation matrix which improves the loading capacity for oils, flavors, pharmaceuticals and the like. The matrix is comprised of maltodextrin and hydrogen octenylbutanedioate amylodextrin or its equivalent. The formulation improves the extrusion processability of the drug and enables high levels of active agent to be incorporated into the dosage form.

U.S. Pat. No. 4,678,516 to Alderman et al. teaches the formation of sustained release dosage forms utilizing a gel matrix comprised of hydroxypropyl methyl cellulose (HPMC) and a major amount of a plasticizer in which the active pharmaceutical is dispersed. Suitable plasticizers include low molecular weight polyols such as ethylene glycol, propylene glycol, polyethylene glycol and the like. The plasticizer is employed to render the matrix thermoformable and comprises a major amount thereof, i.e., at least 30%. The active agent must be heat stable however, so that it is capable of being heated to a temperature sufficient to prepare a gel matrix from the HPMC and the plasticizer without being rendered inactive.

PCT Appln. No. WO 83/00091 teaches the formulation of a polymeric diffusion matrix for the sustained release of water insoluble cardiovascular drugs such as 5-[(3,4-dimethoxyphenyl ethyl)methylamino]-2-(3,4 dimethoxyphenyl)-2-isopropyl valeronitirile. The matrix is comprised of a polar plasticizer, polyvinyl alcohol (PVA) and polyvinylpyrrolidone (PVP) in ratios of about 2:1:1 respectively. The cardiovascular pharmaceutical matrix is particularly useful in transdermal formulations wherein the drug is delivered at a constant sustained rate across the skin.

The present invention does away with the need for elaborate chemical matrices and increases the bioavailability of water insoluble drugs through the formation of a solid pharmaceutical dispersion. The dispersion is formulated without the need of using organic solvents or melting temperatures of drugs (fusion) which would otherwise decompose many drugs which do so at or near their melting temperature.

SUMMARY OF THE INVENTION

The present invention is a novel pharmaceutical solid dispersion and the process for its preparation whereby generally water insoluble drugs are combined with a carrier polymer such as polyvinyl pyrrolidone (PVP) without the need for organic solvents and/or high fusion temperatures. The process utilizes a vehicle such as polyethylene glycol which reduces the transition temperature and facilitates the molecular interaction between the drug and a polymer such as, polyvinyl pyrrolidone (PVP) by partially solubilizing the drug and/or plasticizing the polymer. This allows for a continuous and well controlled processing mode of manufacture.

DETAILED DESCRIPTION OF THE INVENTION

The solid pharmaceutical dispersions of the present invention increase the bioavailability of various water insoluble drugs by increasing their dissolution rates which in turn produce increases in both the rates and extent of the drugs absorption. Hence, the dosage of many solid dispersed drugs can be decreased and it is also believed that due to the increased dissolution and associated rapid absorption may reduce the proportion of the drug that is metabolized presystematically.

Nearly any water-insoluble drug may be formulated in the practice of the present invention so as to increase its solubility and hence its bioavailability. Drugs that are particularly useful in the practice of the present invention are those that decompose at or near their melting temperature since these certainly cannot be formulated into solid pharmaceutical dispersions using the fusion method. Suitable pharmaceuticals include, but are not limited to acetohexamide, ajamaline, amylobarbitone, bendrofluozide, benzbromarone, benzonatate, benzylbenzoate, betamethasone, chloramphenicol, chlorpropamide, chlorthalidone, clofibrate, corticesteroids, diazepam, dicumerol, digitoxin, dihydroxypropyltheophylline, ergot alkaloids, ethotoin, frusemide, glutethimide, griseofulvin, hydrochlorothiazide, hydrocortisone, hydroflumethiazide, hydroquinone, hydroxyalkylxanthines, indomethacin, isoxsuprine hydrochloride, ketoprofen, khellin, meprobamate, nabilone, nicotainamide, nifedipine, nitrofurantoin, novalgin, nystatin, papaverine, paracetamol, phenylbutazone, phenobarbitone, prednisolone, prednisone, primadone, reserpine, romglizone, salicylic acid, spiranolactone, sulphabenzamide, sulphadiamadine, sulphamethoxydiazine, sulphamerazine, succinylsulphathiazole, sulphamethizole, sulphamethoxazole, sulphathiazole, sulphisoxazole, testosterone, tolazoline, tolbutamide, trifluoperazine, trimethaprim and other water insoluble drugs.

Suitable carrier polymers that are useful in the formation of the solid drug dispersion include, but are not limited to, polyvinylpyrrolidone (PVP), high molecular weight polyethylene glycol (PEG), urea, citric acid, vinyl acetate copolymer, Eudragit® acrylic polymers, succinic acid, sugars and mixtures thereof. The carrier of choice obviously is dependent upon the drug to be dispersed but generally the chosen carrier must be pharmacologically inert and chemically compatible with the drug in the solid state. They should not form highly bonded complexes with a strong association constant and most importantly should be freely water soluble with intrinsic rapid dissolution properties.

Preferably, the carrier of choice in most dispersions is polyvinylpyrrolidone (PVP) which is a polymer of the monomeric unit $(C_6H_9NO)_n$ and is a free flowing amorphous powder that is soluble in both water and organic solvents. It is hygroscopic in nature and compatible with a wide range of hydrophilic and hydrophobic resins. Another preferred carrier is a high molecular weight polyethylene glycol such as (PEG) 6000 which is a condensation polymer of ethylene glycol with the general formula $(HOCH_2(CH_2OCH_2))_n CH_2OH$. Polyethylene glycols are generally a clear, colorless, odorless viscous liquid to waxy solid that is soluble or miscible with water.

The surprising and unexpected results of the present invention is the creation of a solid pharmaceutical dispersion comprised of the aforementioned water insoluble drugs and carriers without the need for using organic solvents, fusion (heat) or both (solvent/heat) which are either lengthy and expensive methods or which limit the types of drugs that can be formulated, i.e. heat labile drugs. Surprisingly, it was discovered that the addition of a plasticizer/solubilizer during the mixing of the two components results in a chemical environment that readily lends itself to dispersion formation.

Suitable plasticizers/solubilizers useful in the practice of the present invention include low molecular weight polyethylene glycols such as PEG 200, PEG 300, PEG 400 and PEG 600. Other suitable plasticizers include propylene glycol, glycerin, triacetin, triethyl citrate, and sugar alcohols such as sorbitol, mannitol, and mixtures thereof. Optionally, a surfactant such as Tween 80 may be added to facilitate wettability within the formulation.

The water insoluble drug of interest is first blended with the carrier using any appropriate mixer in a drug/carrier ratio of from about 1:9 to about 5:1 respectively, based upon a percentage weight basis. Preferably, the drug/carrier ratio will be approximately 3:1 to about 1:3, respectively. The blend is then transferred to a fluid. bed granulator and a plasticizer such as PEG 400 is dissolved in water with a surfactant such as Tween 80, if necessary. Other suitable surfactants include Tweens 20 and 60, Span 20, Span 40, Pluronics, polyoxyethylene sorbitol esters, monoglycerides, polyoxyethylene acids, polyoxyethylene alcohols and mixtures thereof. Once both ingredients are sufficiently dissolved, the solution is sprayed onto the powder blend in the fluid bed granulator under specific conditions. The resultant granulation is transferred to a container and fed into a high intensity mixer such as a twin screw extruder with at least one, and preferably more than one heating zones. The mixture is then extruded at appropriate temperatures depending on the heat stability of the drug until a solid dispersion is collected as an extrudate which is then transferred to a drum for milling. The solid pharmaceutical dispersion is then ground into a powdery mass and further prepared in a tablet or capsule form which may be optionally coated with a film such as hydroxypropyl methyl cellulose if desired.

The following examples are given to more particularly set forth and teach several specifics of the present invention. It must be remembered that they are for illustrative purposes only and should not be construed in a manner that will limit the spirit and scope of the invention as recited by the claims that follow:

EXAMPLE 1

Romglizone, whose chemical name is (+)-5-[4-(6-hydroxy-2,5,7,8-tetramethylchroman-2-ylmethoxy)-benzyl]-2,4-thiazolidinedione, is a novel insulin-sensitizing drug being developed for the treatment of non-insulin-dependent diabetes mellitus. The chemical structure of the drug is as follows:

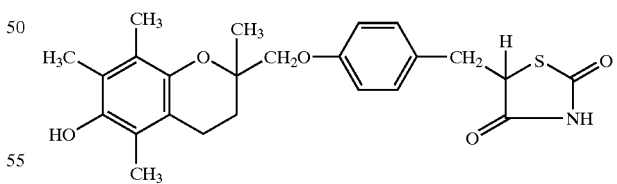

The drug is practically insoluble in water. Its solubility slightly increases as the pH of the aqueous media increases. In vivo studies involving animal models showed that the drug has poor bioavailability when administered in its original crystalline form. In contrast, when an equivalent solid dispersion of the drug in polyvinylpyrrolidone (PVP) was given, the bioavailability of the drug improved significantly.

Romglizone (500 gm.) and polyvinylpyrrolidone (PVP) (300 gm.) were blended in P-K blender (Make, Model) for eight (8) minutes and subsequently transferred to a fluid bed granulator. Simultaneously, a surfactant such as Tween 80 (30 gm.) was dissolved with polyethylene glycol 400 (75 gm.) in a sufficient amount of water for complete dissolution. The Tween/PEG/H$_2$O solution was then sprayed onto the drug/PVP blend in a Roto-Glatt GPCG-5 fluid bed granulator at 36–40° C. until the solution is exhausted. The resultant granulation was then fed into a twin screw extruder with four heating zones set at 125° C., 125° C., 125° C. and 115° C. respectively. The solid dispersion is extruded at a rate of five gms/sec at a head pressure no greater than 5,000 p.s.i. and collected in a drum containing a dessicant such as selica gel. The collected extrudate was then milled using a standard mill such as a Fitzmill to produce a fine powdery mass of the Romglizone solid dispersion.

EXAMPLE II

A batch of solid pharmaceutical dispersion comprising Romglizone was made according to the procedure set forth in Example I using the following materials and proportions. Values given refer to the amount of ingredients in a single tablet.

| | |
|---|---|
| Romglizone | 200.00 mg |
| Polyvinylpyrrolidone | 120.00 mg |
| Tween 80 NF | 12.00 mg |
| Polyethylene glycol 400 NF | 30.00 mg |
| Purified H$_2$O USP | 42.60 mg |

EXAMPLE III

The solid phamaceutical dispersion of Example II was further processed into a tablet core by first thoroughly mixing approximately 362.0 gm. of the milled material with 10.00 mg. of Cab-O-Sil. The resultant mixture was then discharged into a P-K blender and the following materials were then added.

| | |
|---|---|
| Talc USP | 4.00 mg. |
| Microcystalline Cellulose NF | 29.00 mg. |
| Low substituted Hydroxypropyl Cellulose (L-HPC) | 120.00 mg. |

The materials were tumble blended for approximately ten (10) minutes after which a portion of the blend was discharged into a plastic bag. Magnesium stearate (5.00) gm. was added to the contents of the bag and the ingredients were mixed well. The mix was then passed through a No. 30 U.S. standard mesh screen, and added to the main blend. The mixture was again tumble-blended for an additional three minutes. The final blend was then compressed into tablet form using a standard capsule-shaped plain punch known in the art. The tabletted solid dispersion may then be optionally film coated with hydroxypropyl methylcellulose using a standard pan coating apparatus.

What we claim is:

1. A process for the preparation of a poorly water soluble drug in solid dispersion comprising:
    a) blending a poorly water soluble drug with a solvent-free carrier, said solvent-free carrier selected from the group consisting of polyvinylpyrrolidone, high molecular weight polyethylene glycols, urea, citric acid, vinyl acetate copolymer, acrylic polymers, succinic acid, sugars and mixtures thereof;
    b) dissolving a surfactant selected from the group consisting of Tween, Span, Pluronics, polyoxyethylene sorbitol esters, monodiglycerides, polyoxyethylene acid polyoxyethylene alcohol and mixtures thereof, and a plasticizer/solubilizer selected from the group consisting of low molecular weight polyethylene glycol, propylene glycol, glycerin, triacetin, triethyl citrate, sugar alcohols and mixtures thereof, in water;
    c) spraying the surfactant-plasticizer/solubilizer solution onto the drug/carrier mixture in a fluid bed granulator; and
    d) milling the extrudate to a powdery mass of the solid drug dispersion.

2. The process of claim 1 wherein said granulation is extruded at a temperature less than the decomposition point of said drug.

3. The process of claim 2 wherein said drug and carrier are mixed in ratios of from about 1:9 to about 5:1 respectively, on a percent weight basis.

4. The process of claim 3 wherein said drug and carrier are mixed in a ratio of from about 3:1 to about 1:3 respectively, on a percent weight basis.

5. The process of claim 1 wherein the drug is 5,14-(6-hydroxy-2,5,7,8-tetramethylchroman-2-ylmethoxy)-benzyl-1,2,4-thiazolidinedione.

6. The process of claim 1 wherein the carrier is polyvinylpyrrolidone.

7. The process of claim 1 wherein the carrier is polyethylene glycol.

8. The process of claim 1 wherein the plasticizer/solubilizer is low molecular weight polyethylene glycol.

9. The process of claim 1 wherein the solid dispersion is extruded at a rate of 5 grams/second.

10. A process for the preparation of a poorly water soluble drug in solid dispersion comprising:
    a) blending the poorly water soluble drug, 5,14-(6-hydroxy-2,5,7,8-tetramethylchroman-2-ylmethoxy)-benzyl-1,2,4-thiazolidinedione, with a solvent-free carrier, said solvent-free carrier selected from the group consisting of polyvinylpyrrolidone, high molecular weight polyethylene glycols, urea, citric acid, vinyl acetate copolymer, acrylic polymers, succinic acid, sugars and mixtures thereof;
    b) dissolving a surfactant selected from the group consisting of Tween, Span, Pluronics, polyoxyethylene sorbitol esters, monodiglycerides, polyoxyethylene acid polyoxyethylene alcohol and mixtures thereof, and a plasticizer/solubilizer selected from the group consisting of low molecular weight polyethylene glycol, propylene glycol, glycerin, triacetin, triethyl citrate, sugar alcohols and mixtures thereof, in water;
    c) spraying the surfactant-plasticizer/solubilizer solution onto the drug/carrier mixture in a fluid bed granulator; and
    d) milling the extrudate to a powdery mass of the solid drug dispersion.

11. The process of claim 10 wherein said drug and carrier are mixed in a ratio on from about 3:1 to about 1:3 respectively, on a percent weight basis.

12. The process of claim 11 wherein the carrier is polyvinyl pyrrolidone.

13. The process of claim 12 wherein the carrier is polyethylene glycol.

14. The process of claim 13 wherein the plasticizer/solubilizer is low molecular weight polyethylene glycol.

15. The process of claim 14 wherein the solid dispersion is extruded at a rate of 5 grams/second.

* * * * *